United States Patent [19]

Wess et al.

[11] Patent Number: 5,081,984
[45] Date of Patent: Jan. 21, 1992

[54] POSITIONING A PATIENT FOR LITHOTRIPSY

[75] Inventors: Othmar Wess; Pavel Novak, both of Munich; Klaus Mechnich, Wessling; Reiner Schultheiss, Eching, all of Fed. Rep. of Germany

[73] Assignee: Dorinier Medizin Technick GmbH, Fed. Rep. of Germany

[21] Appl. No.: 492,687

[22] Filed: Mar. 13, 1990

Related U.S. Application Data

[63] Continuation of Ser. No. 124,120, Nov. 16, 1987, abandoned.

[30] Foreign Application Priority Data

Nov. 14, 1986 [DE] Fed. Rep. of Germany ....... 3638953

[51] Int. Cl.⁵ ............................................. A61B 17/22
[52] U.S. Cl. ................................................ 128/24 EL
[58] Field of Search .................................. 128/24 EL; 600/127–128; 378/68–69, 195, 198, 65; 318/26, 467; 5/81 R

[56] References Cited

U.S. PATENT DOCUMENTS

| | | | |
|---|---|---|---|
| 2,860,293 | 9/1955 | Salamonovich | 318/626 |
| 3,795,853 | 3/1974 | Whitehouse | 318/626 |
| 3,995,205 | 11/1976 | Klees | 318/626 |
| 4,230,129 | 10/1980 | La Veen | 128/24 A |
| 4,356,577 | 11/1982 | Taylor et al. | 5/81 R |
| 4,604,560 | 8/1986 | Inagaki et al. | 318/626 |
| 4,610,249 | 9/1986 | Makofski et al. | 128/328 |
| 4,705,026 | 10/1987 | Chaussy et al. | 128/24 EL |
| 4,763,652 | 8/1988 | Brisson et al. | 128/24 A |
| 4,796,613 | 1/1989 | Heumann et al. | 128/24 EL |
| 4,811,725 | 3/1989 | Grosser | 128/24 EL |

FOREIGN PATENT DOCUMENTS

| | | | |
|---|---|---|---|
| 0168559 | 1/1986 | European Pat. Off. | 128/328 |
| 2238706 | 2/1974 | Fed. Rep. of Germany . | |

*Primary Examiner*—Francis Jaworski
*Assistant Examiner*—Scott R. Ahers
*Attorney, Agent, or Firm*—R. H. Siegemund

[57] ABSTRACT

Apparatus for positioning the body of a patient in relation to equipment for contactless comminution of concrements such that the focal point of equipment is made to coincide with a concrement; the patient who lies on a rest which is moved with the patient on it in a longitudinal direction, tilted about it, and moved also laterally and in a direction that is transverse to the longitudinal and lateral directions of movement; a water filled cushion with controlled water level is adapted for interpositioning between the equipment for comminution and focusing, and the patient, a plurality of differently oriented X-ray beams are provided for locating a concrement in the patient and images are marked through a light pen or the like on X-ray monitors; a control provides for homing-in the rest in relation to the comminution equipment such that its focal point coincides with the concrement as previously detected.

10 Claims, 4 Drawing Sheets

| | TABLE POS. | | | |
|---|---|---|---|---|
| COLLISION (PROTECTION) | ON | | | |
| COUPLING WATER CUSH. | MANUAL | | | |
| POSITION - CUSH. FOLLOW UP | MANUAL | | | |
| LIGHT PEM POS. ACQUIS. | LOCALIZE OBJE. ON MON 10 | | | |
| | LOCALIZE OBJE. ON MON 12 | | | |
| AUTOMATIC TARGET ACQU. | MANUAL | | | |
| DES. COORDINATES | X | Y | Z | ~ |
| ACTUAL COORDINATES | X | Y | Z | ~ |
| CUSHION POS. | X | Y | Z | ~ |

START PROG.
DATA REST.
PATIENT
THERAPY

Nov. 16, 1987, now abandoned.

POSITIONING A PATIENT FOR LITHOTRIPSY

This application is a continuation of Ser. No. 07/124,120, filed Nov. 16, 1987, now abandoned.

BACKGROUND OF THE INVENTION

The present invention pertains to automatically positioning a patient, who lies on a rest, such that the patient can assume an exactly predetermined posture and position particularly as far as certain body parts are concerned and in relation to particular equipment.

In particular, the invention relates to the automatic positioning of a patient so that a concrement in his/her body is placed into the focal point of a device provided for the comminution of such a concrement.

U.S. Pat. No. 3,942,531 corresponding to German printed patent application 23 51 247 describes a device including a focusing chamber for the comminution of concrements in the body of human beings. The focusing chamber is a portion of and pertains to a rotational ellipsoid that outlines and delineates the interior chamber wall. Such an ellipsoid has two focal points. Shock waves are produced through spark discharge at one of the focal points, and these shock waves are focused by the device in the second focal point. The chamber is filled with a liquid serving also as a coupling fluid to couple the body of the patient to the focusing chamber. The construction is chosen so that the concrement to be comminuted is situated in that second focal point of the ellipsoid. The shock waves are produced through an underwater arc discharge having two electrodes across which a capacitor discharges. As the discharge is ignited, shock waves are produced in the first mentioned focal point of the rotational ellipsoid. The ellipsoid is carefully constructed to permit a high concentration i.e. near pointlike concentration of shock waves in the second focal point. The pressure amplitudes may exceed 1 kbar and the duration of a shockwave pulse is less than 1 microsecond. A high concentration of shockwave energy is made possible on account of the high degree of focusing produced by the ellipsoid while on the other hand the shock waves as they converge towards the concrement and pass through normal tissue, affect that tissue only insignificantly. Following the destruction of the concrement and its pulverization or breaking up the concrement e.g. into grit, that grit will be discharged from the body by normal physiological process. This is particularly true in case of kidney stones.

It is of course apparent that the aforementioned method will function properly only if one knows exactly where that concrement is situated, so that in fact the device can be positioned such that the above mentioned second focal point coincides with that point in the interior of the body of the living being in which a concrement appears to have lodged. It is, therefore, necessary to determine the position of such a stone ahead of time i.e. prior to launching comminuting shockwaves. In the past one has used X-rays, particularly two separate X-ray beams, for obtaining spatial coordinate values of the concrement once the patient has assumed a particular position.

German patent 34 26 398 (see U.S. Pat. No. 4,936,291) describes a system by means of which a concrement is located, and the patient is positioned under utilization of a combination and, particularly, correlation of an X-ray locating system and an ultrasonic locating system. Here particularly the ultrasonic locating system will continuously monitor the position of the kidney stone, even after it has originally been located, and signals are provided and steps are taken to fix the location of the stone as far as external equipment is concerned.

It should be observed that when the patient is breathing the stone undergoes a certain movement and, therefore, may oscillate around a particular point at the rate of breathing. The second focal point of the rotational ellipsoid can be made to coincide with that particular zero point around which the kidney stone oscillates, and continuous observation of the stone as it moves and oscillates permits manual triggering of the shock waves right when the stone passes through the focal point. This is done through the ultrasonic system and only occasionally is the X-ray system used to determine the resolution and the extent any comminution of a kidney stone was successful. The automated or quasiautomated tracking and following of the equipment in relation to the kidney stone must require that it occurs in the ultrasonic section plane. Another locating device may be provided and shifting within the ultrasonic section plane may be made visible on a screen. One may locate and identify on a monitoring screen a kidney stone. The screen may simulate the ultrasonic section plane. Next, a light pen may be used on the screen to identify a particular point namely the point where the stone is located, and now computer operated functions may ensue.

The Munich Medical Weekly (Muenchner Medizinischen Wochenschrift, 125, 1983, No. 8, pages 151-155) describes a device for comminuting kidney stones through shock waves. The concrement is to be placed in the focal area of a bundled and focused shock wave. This position is obtained through a motor driven positioning device which is manually operated and controlled by the attending physician. Moreover, this device as described shows that the location of the stone is monitored by the physician through two independent X-ray systems.

German printed patent application 32 20 751 discloses a similar device which includes either two independent X-ray systems or two independent ultrasonic systems used in conjunction with a positioning device being independent from the foregoing equipment and operated by the physician. Further patents of interest are U.S. Pat. Nos. 4,669,483, 4,552,348, 4,938,232, Ser. No. 942,251 and U.S. Pat. No. 4,705,026.

DESCRIPTION OF THE INVENTION

It is an object of the present invention to improve recognition and acquistion of locating a concrement to be comminuted as fast as possible, bypassing any operating personnel and to obtain representation in four axial directions, ultimately to place the second focal point of a lithotripter that includes rotational ellipsoid, such that this second focal point is made to coincide with the concrement to be comminuted; the principal goal in mind is that the patient as well as the personnel must not be exposed excessively to X-rays, at the very least the X-ray must be held very low.

Another object and purpose of the invention is to ensure a transition and interface between water and the patient without the inclusion of bubbles or the like and it must be ensured that this connection is maintained throughout.

In accordance with the preferred embodiment of the present invention a lithotripter is suggested which includes a positioning device which moves the located concrement by moving the rest on which the patient lies together with the patient, in at least three axes; the first one extends along the body and this movement is from feet to head or vice versa. The second direction is taken in regard to the normal position and posture of the patient described, that being a movement to the left and to the right; and the third coordinate is a direction transverse to both these aforementioned directions. Moreover, an automatic follow-up is provided for the water cushion level to ensure air bubblefree coupling of that cushion to the patient's body. The cushion is established by the water generally and is placed between the skin of the patient and the shock wave generator/focusing device; the water serves as a coupler fluid between the lithotripter itself and a membrane that closes off the submerged spark generator of the lithotripter by means of which the shock wave production is initiated.

The patient can be assumed to have been placed on a rest which in turn can be placed either onto a vehicle, a cart or the like to wheel the patient into the treatment room. The rest with the patient lying on it, can also be placed on a treatment table, whereby, so to speak the position of the patient as such and particularly of the concrement in him has the same position in relation to the vehicle as it has now in relation to the treatment table. Patient movement on the rest and through the vehicle is thus equivalent to a movement of coordinate system. Thus, even though there is physical relocation of the patient his/her position are such that upon the aforedescribed movement the concrement is merely being relocated in a known fashion without displacement in relation to the translated coordinate system. In other words, the particular positions are indicated by LED-s which indicate specifically the instantaneous position of the equipment. Involved is a movement along the three axes mentioned earlier and a fourth motion is provided along a tilting axis. The purpose of that tilting is to avoid "shading" of the concrement by ribs or the spine. In addition the X-ray coordinates, horizontal as well as vertical are ascertained whereby particularly any horizontal movement of the concrement actually moves only within the plane of one of the monitors or the other.

In treatment position the patient rests with his back on a water cushion (see e.g. application Ser. No. 942,251). Between the cushion and the patient there is an ultrasonic coupling layer which is a pasty gel and which couples the casing of the cushion directly to the skin of the patient to avoid the forming of cavities, bubbles or the like (see also U.S. Pat. No. 4,805,600). If bubbles are present a wiper may remove them (see e.g. U.S. patent application Ser. No. 942,259). This method is preferred because it can be practiced in a simple fashion, and there is no negative influence exerted on the equipment; particularly, nothing impedes the propagation of shock waves. The level of the water cushion can be raised or lowered by key operation from control panel if such is desired.

In order to visualize later the concrement on an X-ray screen the positioning table is manually moved, i.e. through manually operated servo motors, until the concrement is visible on both screens. The level of the water cushion is manually or automatically caused to follow, through computer operation to maintain coupling of the lithotripter to the patient, and in dependence upon the movement of the positioning table. This way the shockwave generation is ensured. The contact necessary for shock wave treatment as between the patient and the cushion will not be interrupted on account of the positioning procedure and the ensuing movement.

Subsequent to the foregoing a locating procedure is carried for finding the concrement. This procedure is computer operated, and is provided for ascertaining specifically the position of the concrement. The locating operation is carried out through crossing X-ray systems, i.e. under utilization of two, intersecting X-ray systems. Each of these systems is oriented in an angle to the respective other one, in that the two projection planes have an angle in relation to each other one. These angles can vary but they can be held fixed. The required projection coordinates, as far as X-ray projection is concerned, are ascertained by means of a monitor and video image device pertaining to the X-ray equipment. First, an X-ray image is taken to ascertain the condition of the concrement and an image of concrement is made visible on both monitors. Next, a light pen (wand) system is activated. The concrement is positioned somewhere in the projected area on the screen. Next, the second monitor is turned off and the user will mark the position of the concrement through the light pen. If the ascertained values are correct within particular equipment limits this monitor is also turned off, and the user-technician will enter the position into the second monitor. In an alternative version one may dispense with the initial turn-on of both monitors, and one starts out with having only one X-ray system turned on for a little and the other by itself thereafter.

The light pen has a pressure responsive feeler at its tip and is operated with the pen touching the image on one of the screens i.e. the respective screen itself. The resulting feeler response starts an electronic positioning device provided for acquiring positional data, here the location of the light pen. A period of time is ascertained which the electron beam has available to move in accordance with a regular video, scan beginning e.g. at a corner of the monitor, until reaching the particular location where the light pen touches the screen. This scanning usually follows the conventional television line raster.

The electron beam's position will accordingly be located through the position of the light pen, particularly by means of a photodiode in the tip of that pen a threshold discriminator is connected to that diode. One or two counters are used for ascertaining the time. In the one counter version, that counter just tracks the time from the beginning of a field (frame) scan. However, the two counter version permits operation at a larger accuracy. One of the counters acquires the line number and the other one just cumulatively counts from the beginning of a line until a line pen signal is detected on that line. The accuracy can be improved further through measuring, on a running basis, the entire line length which is then used for normalizing any in-line period. This procedure compensates any variations in line frequencies.

The thus acquired virtual coordinates in terms of line number and line scan time, and counting from the beginning of a line up to the location of the light point are values which in a computer and using conventional algorithm, can readily be used to ascertain a coordinate value in relation to a point of origin which for example is located or situated in the center of the monitoring screen. In other words, the attending physician uses the light pen to mark on one (or both) X-ray monitors a location that is expected to be the location of his diagnozed concrement, and now that location is referred to the equipment bearing in mind that the X-ray locating system with its center and center beam is a well defined system and in fact establishes coordinates in relation to which the light pen marking denotes the concrement. Having done that, the position inputting operation is completed.

Coordinate inputting generally as described may be obtained with other means such as the so called tracking ball, a joystick or a mouse. Here it may be advisable to project a haircrossing onto the screen, or an arrow or a distinctive cursor or the like.

Thereafter, i.e. after the concrement location has been illustrated on the screen and e.g. through manual key operation automatic positioning is initiated. The computing facility responds to the coordinates ascertained through the light pen (or any of the other inputting devices) and calculates the mathematical relationship between the position of the monitor and video screen coordinate system, on one hand, and the spatial coordinate system of the concrements of the patient on the rest on the other hand. The reference point or coordinate origin in this case is, as far as equipment is concerned, the known geometric second focus of the rotational ellipsoid as defined above.

The first focus, within the present context, is always the focus of the reflector in which the shock waves are generated by means of spark discharge, and the second focus of that reflector is exactly that, a second focus of the rotational ellipsoid serving as the reflector and into which shock waves are focussed when generated by and in the first focus. Now, the geometric parameters of the second focal point are used as reference coordinates. That second focal point has a definite position vis-a-vis the patient or the rest. The master computer will provide control signals such that the concrement in the patient and through motion of the positioning table on which the patient lies and control table is made to coincide with the coordinates of the this second focal point for the shock wave.

Each of the coordinate axes indicated above is associated with an indexer that is a servo computer which signals back to the master computer the respective state, namely the position of the equipment such as the rest vis-a-vis the respective axis. This indexing computer will ultimately control the movement of the patient and of the rest on that axis. The coordinates of tracking transducers are monitored and ascertained; as the device homes-in on any desired coordinate as for the specific axis is concerned, the motion is slowed down or stopped. Accuracy should permit that after all three (or more, infra) axis-movements have been completed, indeed the concrement is situated and located in the second focal point $F_2$.

Three commands can be executed with regard to each axis and by the respective indexing motions. (i) Movement at constant speed generally; (ii) motion towards a predetermined coordinate point and stopping therein; (iii) interrogating the equipment status. The motion of the patient rest is speed controlled with a max speed of about 10 mm/s whereby acceleration and deceleration occur preferably along graduated slopes and ramps. Through coordination of the various drives operating in relation to the various axes, one can in fact carry out any kind of movement, of course within practical limit, and along any kind of trajectory.

For example it may be of advantage to use an isocentric motion pattern to home in, in the above defined sense. The various inputs and operations will be indicated to be observed by the user and operator, using for this purpose a separate monitor for the computer. The instantaneous input may be highlighted on the screen so that the operating person knows where the positioning actually is in any given moment. The master computer runs through the individual steps for positioning by means of the indexing motors but the individual operating modes may be selected by the user from within a menu as it appears on the screen. In addition protective functions for the positioning operations are provided, such as responding to touching of the ellipsoid edge by the patient so that any kind of patient can be treated. Moreover, desired coordinate value will be displayed on the screen as part of the menu in addition to the actual patient-table coordinates as well as the actual water cushion level.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 2 is an example of the operator's panel manual as can be seen on the monitor of the panel;

Proceeding now to the detailed description of the drawings, FIG. 1 shows a first central and control computer 2 being a master controller to which are connected, as input-output units, an operator terminal 4 with the usual panel and monitor, a manual override control 6 that has a separate function but physically it may be a part of the panel 4; and a light pen-measuring and data acquisition system 8. The light pen system 8 is connected to two X-ray monitors 10 and 12 as well as the respective X-ray receiving systems 10" and 12". Reference numerals 10' and 12' denote the X-ray sources.

Figure 1:
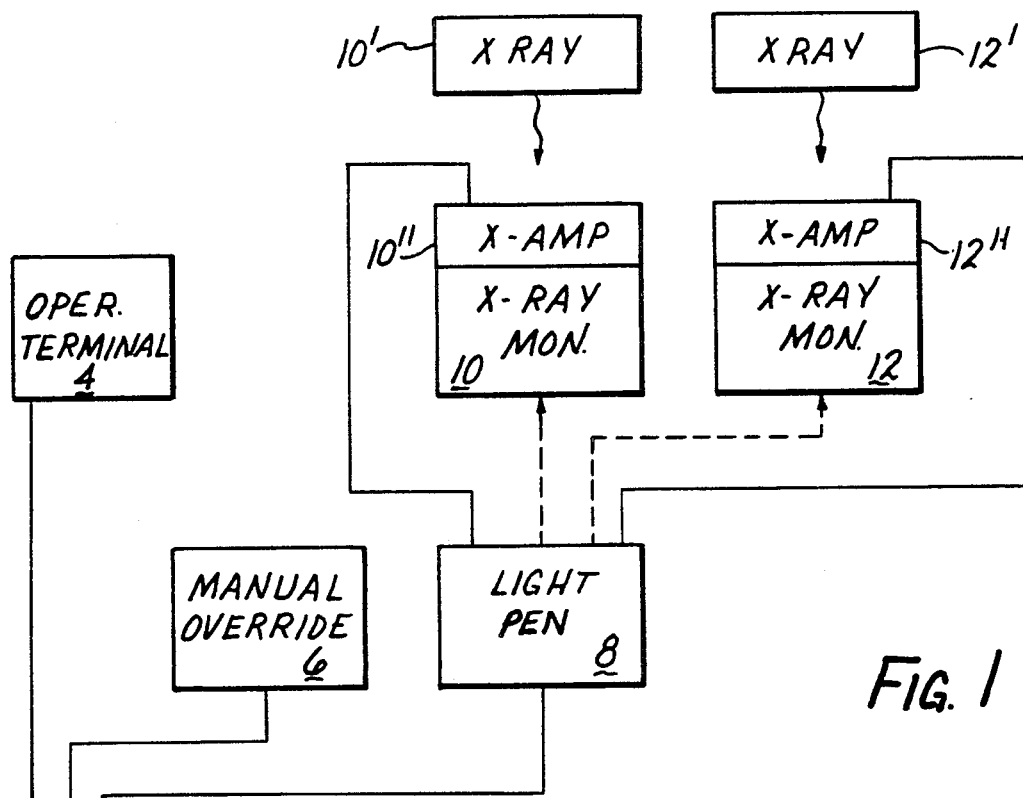
FIG. 1 illustrates a block diagram for a positioning control device in accordance with the preferred embodiment of the present invention for practicing the best mode thereof.
Figure 1:
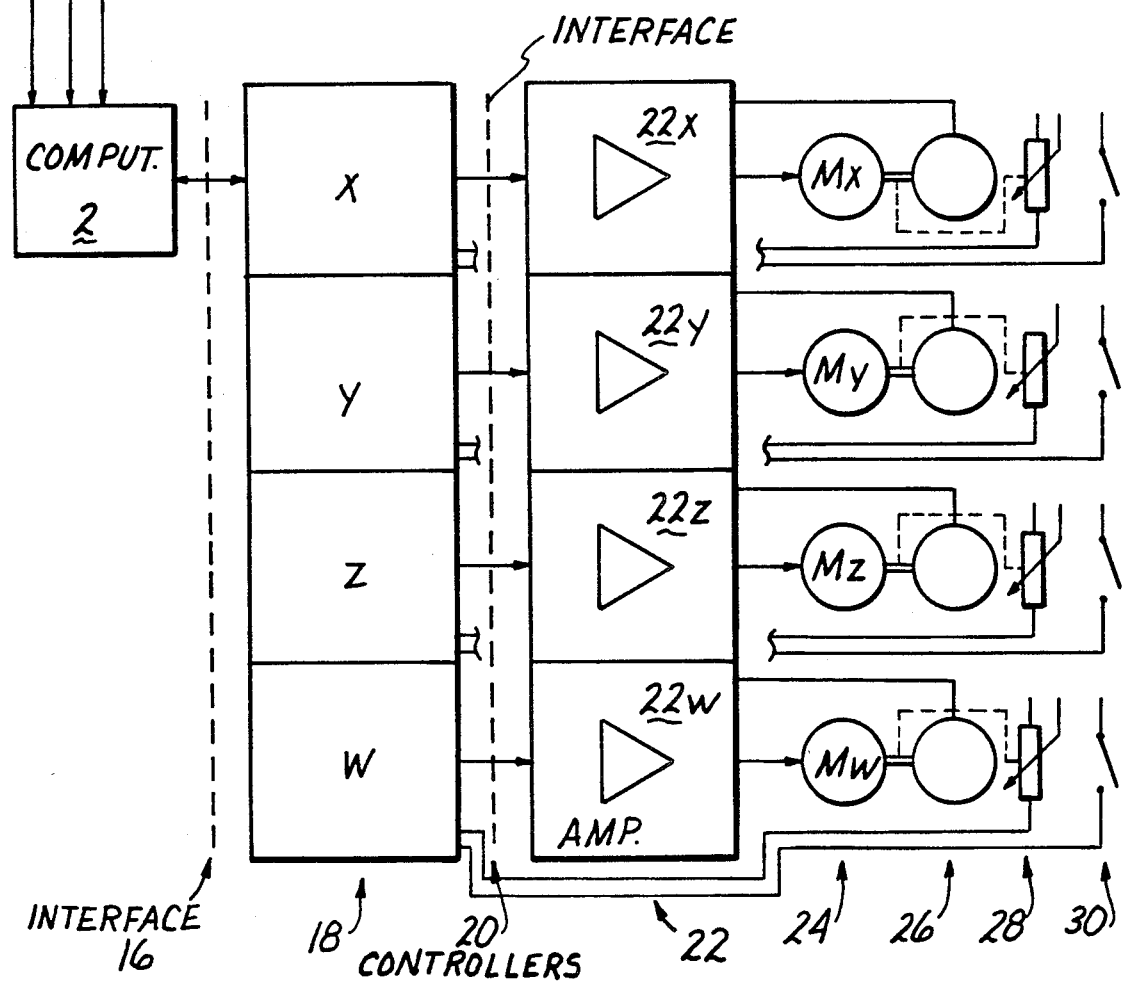

A first interface circuit 16 provides for the transmission of commands from the master controller 2, to four independently operating indexing computers or controllers designated collectively by 18 and further identified by the axes x,y,z,w to indicate that motion is provided along axes x,y, z and in a tilting direction w around axis x. The respective motion is carried out by a group of motors 24 individually identified by Mx, My, Mz, Mw. The four controllers 18 provide the servo operation for position controlling each of the motors 24 separately and in feedback configuration. The master controller 2 provides a common control signal for indicating to each of the motors 24 a representation, to where to place the patient rest as far as motion on the respective axis (x,y,z,w) is concerned. The patient rest may be constructed as shown e.g. in U.S. Pat. No. 4,705,034 issued Nov. 10, 1987 or the other references mentioned above.

The second interface 20 establishes a connection between the four indexing computers or controllers 18 with power output stages 22 (22x, 22y, 22z, 22w) which in turn operate and drive the motors 24 thereof; as already stated there are four motors Mx, My, Mz and Mw corresponding to the four axes (x,y,z,w). The motor shaft in each instance as far as providing turning operation is concerned and to be explained more fully below, is connected to a shaft encoder 26. There are four encoders being in each instance an optical encoder or any other path tracking device, a transducer, tachometer, or resolver, which, on an incremental, high resolution basis tracks the motion of the respective motor. The encoders 26 provide signals which are directly used for motor control in the power end stages 22 immediately as far as feedback is concerned, and also through the respective controllers 18 for determining tracking and indicating to the equipment the actual position of the motion devices as they are related to particular axes. These encoders 26 and particularly their motor shafts are connected in addition to absolute value yielding transducers 28, which give exact position values to the controllers 18. To the extent necessary the indexing computers will communicate that information to the master control computer 2.

Mechanical limit switches 30 are provided along the axis and in end position of movement obtained by the motions along these axes (x,y,z,w). These switches indicate to the computers or controllers 18 and to the power stages 22 directly that further motion in the particular direction is no longer possible because what is being moved has reached an end position. These are actual physical limiters operating in addition to software limits which, independently from the physical limitation provide for limitations on attainable movement. Details will be explained more fully below. In each case the effect of a response is to turn off the respective power stage 22 completely and immediately to bring whatever motor is available to a full stop in order to avoid any damage. Such damage may be to the equipment but also to the patient.

The calculating system as well as the X-ray system are electrically (potential) separated from the light pen system so that any potential transfer and voltage differences will not become effective anywhere.

FIG. 2 illustrates an operator's menu as it may appear on the monitor of terminal 4 as shown in FIG. 1. The menu will be run through by the computer 2 automatically, line by line, and the respective relevant information of immediate actuality is highlighted. Moreover, the desired coordinates as far as the concrement position is concerned, as well as the coordinate system of the focal point F2 in concrement and, finally, the level of the water cushion are also indicated. The desired value coordinates as well as the actually existing coordinates have to agree at a particular point in time so that the concrement is in the right position when a shock wave is being released and generated. Through the coordinates one can also ascertain indirectly whether and where the positioning devices have reached its limit position anywhere.

The positioning device as proposed here in fact shortens the needed time to locate a concrement in that locating and positioning in the automated control operation are in each instance one shot operations. The positioning is to a large degree independent from the operating personnel. The only genuine human input is actually a medical diagnosis; the physician has to identify on the X-ray screen 10, 12 the location of the concrement. That is to say, as the physician touches a point on the screen 10/12 with the light pen, the system "assumes" that this is the desired point of the concrement location, and the equipment homes in on it. This is an important safety feature because once that desired point is identified, the X-ray equipment can be turned off and that minimizes in fact the X-ray load on the patient but also on the operating personnel at large so that the overload safety aspects are increased. Moreover, erroneous positioning is in fact excluded once a concrement has been recognized by a trained person and within the prescribed limits (infra).

From an overall point of view the treatment time can be shortened and the equipment can be used longer and for a larger number of patients. The water cushion automatically tracks any patient movement and that maintains coupling between the patient and the cushion membrane. Inputting the concrement position in the alternative can be carried out through a touch screen. A touch screen is a particular device placed in front of a video screen with an infrared lattice or a particular pressure sensitive foil. The position can be indicated simply by touching the screen i.e. the device with a finger.

In order to meet of all the required and desired safety factors, including any demands made on account of safety rules, it may be required to minimize coupling between X-ray equipment and use calculator as well as the measuring system. For this purpose one needs the device of the invention in lieu of complete digitization of any X-ray image, the invention uses just the filtered out video synchronous and time synchronous pulses extracted from the X-ray image.

Figure 3:
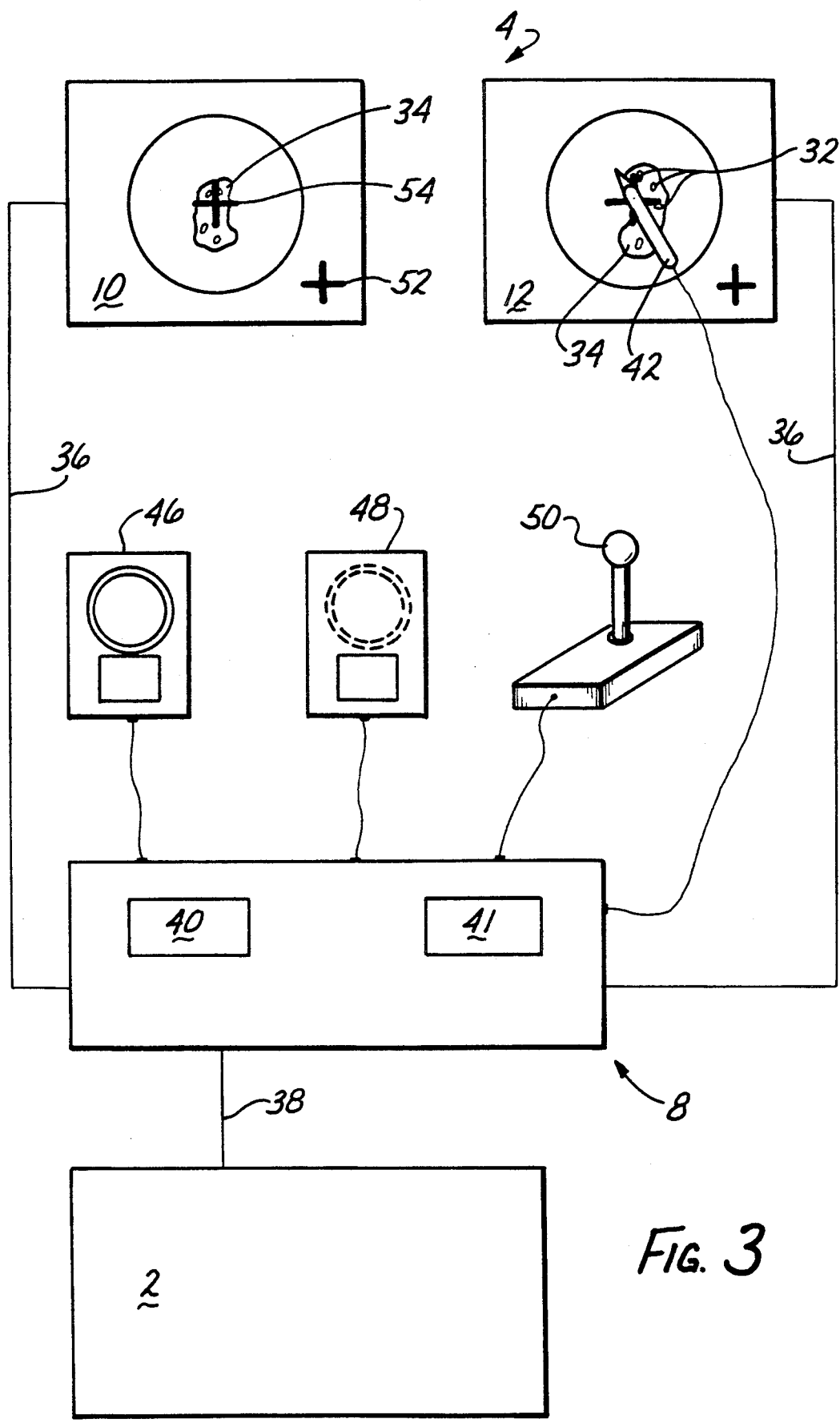
FIG. 3 is a schematic illustration of a light pen measuring, indicating and inputting system showing additionally alternative input devices.
Figure 4:
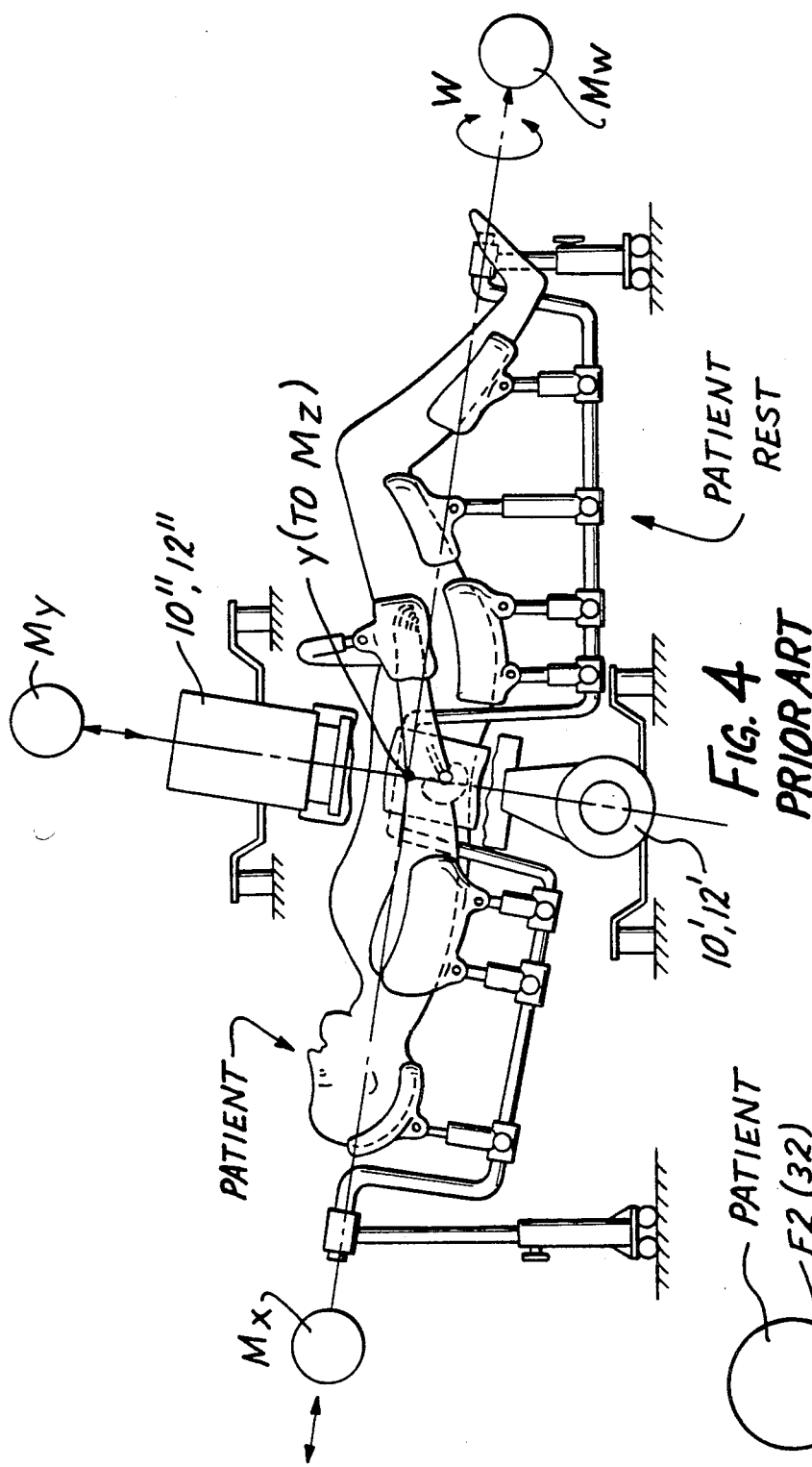
FIGS. 4 and 5 are modified drawings from U.S. Pat. No. 4,705,026 as modified background.
Figure 5:
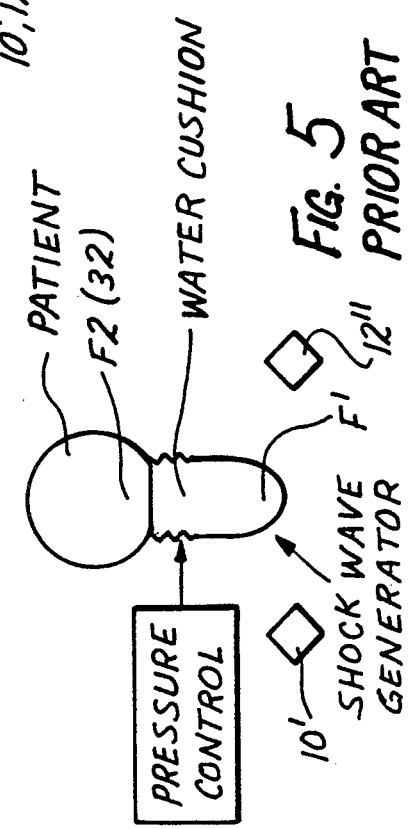

FIG. 3 includes schematically the coordination of the light pen measuring system 8 for acquiring the coordinates of actual location of concrements such as 32. The two X-ray monitors 10 and 12 will image the concrements 32 as well as the kidneys 34. Monitor 10 and 12 are connected to the light pen system 8 via connectors 36. Another electrical connection 38 connects the light pen system 8 to the main computer 2. The light pen system 8 includes two counters 40 and 41 for determining screen coordinates where the pen has touched the screen. The light pen 42 itself is, of course, connected to and is a part of the system 8. The pen 42 has a tip which includes a pressure monitor and switch 44. In addition, there is a light receiver (not indicated).

Alternatively one can use a tracking ball 46, a mouse 48 or a joystick 50. They all can be part of the same system and can be used alternatively. They are connected to and are a part of the measuring system 8 and provide corresponding coordinates values. In the case of a tracking ball, a mouse or a stick one needs also hairpin as well as a central cross hair 54 a monitor screen 10 or 12 has anyway.

In order to guarantee safe and secure position of the patient a number of safety functions and precautions are integrated in the system.

(a) Function tests on operational start up are carried out through the computer 2 in that a movement is introduced i.e. motors 24 are turned on and simulate and run through their ranges while automatically a comparison is made between actual and desired coordinates and any agreement or disagreement agreement is tested. If as a consequence of this test, agreement does not obtain, an appropriate positioning system defect will be displayed on the monitor 4.

(b) All movements which are manually introduced as well as automatically obtained or obtainable positions, are triggered in accordance with the dead man principle i.e. it requires actuation of a particular key by an operator. If the key is not or no longer depressed i.e. released for any reason, the respective motion is stopped automatically.

(c) Certain limits are introduced as far as the source is concerned and with respect to the motion as controlled by the various computers whereby a combined motion in several directions may lead to stopping if for some reason a software limit has been reached.

(d) Analogously, there is a hardware limit (switches 30) as far as motion overrun is concerned. These limits that are provided at the end of the respective displacement paths. Whenever such a limit is reached then the appropriate calculator or even the power source of the equipment turns off the device of controls.

(e) The current supply to a power stage is generally turned on by the calculator and computer 2 only during positioning, if there is no positioning the power simply is turned off.

(f) Motion is triggered only when the respective motion control stages, i.e. controllers 18 do not only receive speed control signals but also an independent enabling signal.

(g) Any signal transmission from and to the respective path transducer 26 is carried out through a wire pair i.e. without the reliance on any connection that is common or to ground.

(h) For inputting the position of a concrement through the light pen system 18 one provides for a number of unique error signal situations.

(h1) "No position input". This kind of error situation appears on the monitor 4 if within 30 seconds following a request made by the operator menu no input has been provided by the light pen system 8(42). This situation implies that there is nothing the user can indicate even though he should indicate.

(h2) "Inaccurate positioning". This indication appears on monitor 4 if the inputted data scatter too widely. As the light pen 42 touches the screen (10 or 12) one will obtain about 10 coordinate pairs which are being ascertained by the counter tracking the light pen 42(8). The range between zero and the maximum value is subdivided into X-groups wherein X is the maximum permissible scatter value divided by 10. The values as ascertained are divided into groups wherein each group covers a certain number range. From the group which covers more than 5 values one will calculate standard deviation as well as the medium or average value. If the standard deviation exceeds 0.01 the above mentioned indication obtains.

(h3) "Positioning input incorrect" is an indication which signifies that all of the coordinate values do not lead to a particular point in space within a sphere of 10 mm diameter.

(h4) "Position not obtainable" will be indicated under the following conditions. The maximum freedom of motion on each axis is about +10 cm. If the respective calculated coordinate is outside of that range this error indication obtains. One can also indicate on the screen in what direction the patient has to be physically relocated on the rest e.g. after a particular limit of motion has been obtained so that the patient is shifted in the range covered by the equipment.

(i) If the desired and the actual coordinate values do not agree with the limits as defined above during automated positioning and are caused e.g. by accidental release of the enabling key, then the following obtains. In order to increase safety after the positioning has been completed a, so to speak, cross check through an X-ray system may be carried out.

The invention is not limited to the embodiments described above but all changes and modifications thereof, not constituting departures from the spirit and scope of the invention, are intended to be included.

We claim:

1. A lithotripter including equipment for the contacless noninvasive comminution of concrements, further including an apparatus for positioning the body of a human being and patient in relation to the equipment for noninvasived comminution of concrements such that a focal point of that equipment is made to coincide with a concrement in that patient, the apparatus including a rest on which the patient is placed, the improvement comprising:

first means for moving said rest with the patient on it in a longitudinal direction being also a longitudinal direction and axis with regard to said patient as so positioned and his/her orientation on the rest;

second means for moving said rest laterally in relation to movement of the first means corresponding to a movement to the left and to the right as far as said orientation of the patient is concerned;

third means for moving said rest in a direction transverse to said longitudinal and lateral directions of movement;

fourth means for tilting the rest about the longitudinal axis;

a water cushion filled with water and adapted for interpositioning between said equipment for comminution and said patient, there being means for controlling the level of the water in said cushion;

a plurality of locating devices, said devices being oriented in directions that are different from each other, for locating a concrement in the patient;

display means connected to the locating devices for visibly indicating the respectively located concrement and separately as to each of the locating devices;

first control means coupled to said locating devices and including means for cooperation with the display means for establishing, in relation to the display on the display means signals, representing coordinate positions for the concrement as visible in the display means and separately for the display produced by each locating devices;

second control means connected to the first control means and to said first, second and third means and operating in response to the signals for homing in said rest in relation to the comminution equipment such that its focal point coincides with the concrement as detected by said locating means, and as identified by the first control on the display means; and means for operating the comminution equipment for the comminution of the detected concrement.

2. Apparatus as in claim 1 wherein at least one of said locating devices is an X-ray device, the X-ray device being turned off after the first control means has identified the concrement position as imaged upon the display means associated with the X-ray locating device.

3. Apparatus as in claim 1 the display including a monitor for visual indication as to what the locating devices detect, to provide a closing loop as between the concrement as depicted on the monitor and the physical location of said focal point.

4. Apparatus as in claim 1 wherein each of said first, second and third means includes a controller, a power stage connected to the controller for being operated therefrom, a motor for driving the first, second, and third means, connected to the power stage and a position feedback means coupled back at least to the respective controller.

5. Apparatus as in claim 4 including a plurality of motion limiting means respectively for stopping the motors in case of override.

6. Apparatus as in claim 1 said display means including at least one monitor, said first control means including a light pen means for cooperation with said at least one monitor.

7. Apparatus as in claim 1 said first control means including a joystick.

8. Apparatus as in claim 1 said first control means including a mouse.

9. Apparatus as in claim 1 said first control means including a tracking ball.

10. Apparatus as in claim 1 including fourth means for tilting said rest about said longitudinal direction.

* * * * *